United States Patent [19]

Ip et al.

[11] Patent Number: 5,360,740
[45] Date of Patent: Nov. 1, 1994

[54] ASSAY SYSTEM FOR DEGENERATIVE MUSCLE DISEASE

[75] Inventors: Nancy Y. Ip, Stamford, Conn.; Peter S. DiStefano, Carmel; Neil Stahl, S. Salem, both of N.Y.

[73] Assignee: Regeneron Pharmaceuticals, Inc., Tarrytown, N.Y.

[21] Appl. No.: 907,680

[22] Filed: Jul. 2, 1992

[51] Int. Cl.$^5$ ............... G01N 33/536; G01N 33/543; G01N 33/566
[52] U.S. Cl. ................................ 436/501; 436/518; 436/536; 436/811
[58] Field of Search .................. 435/7.92, 7.21, 7.5; 436/86, 87, 501, 518, 536, 529, 804, 530

[56] References Cited

U.S. PATENT DOCUMENTS 4,997,929  3/1991  Collins et al. .............. 435/69.1
5,141,856  8/1992  Collins et al. .............. 435/69.1

OTHER PUBLICATIONS

Davis et al., 1991. The receptor for ciliary neurotrophic factor, Science 253: 59–63.

*Primary Examiner*—David Saunders
*Assistant Examiner*—James L. Grun
*Attorney, Agent, or Firm*—Gail M. Kempler

[57] ABSTRACT

An assay system useful for detecting denervated or degenerating muscle by measuring the amount of soluble ciliary neurotrophic factor receptor in body fluids is described.

6 Claims, 2 Drawing Sheets

ASSAY SYSTEM FOR DEGENERATIVE MUSCLE DISEASE

INTRODUCTION

The present invention relates to a diagnostic technique useful for detecting, diagnosing or monitoring neurological and/or muscular diseases, disorders or injuries. The invention provides for an assay system useful for detecting denervated or degenerating muscle by measuring the amount of soluble ciliary neurotrophic factor receptor (CNTFRα) in body fluids.

BACKGROUND OF THE INVENTION

Ciliary neurotrophic factor (CNTF) is a protein that is required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervates the ciliary muscle and sphincter pupillae.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70–73). Furthermore, it has been observed to promote the survival of embryonic chick dorsal root ganglion sensory neurons (Skaper and Varon, 1986, Brain Res. 389:39–46). In addition, CNTF supports the survival and differentiation of motor neurons and hippocampal neurons. (International Application No. PCT/US 90/05241)

Recently, CNTF has been cloned and synthesized in bacterial expression systems, as described in copending U.S. application No. 07/570,651, entitled "Ciliary Neurotrophic Factor," filed Aug. 20, 1990 by Sendtner et al. incorporated by reference in its entirety herein.

In addition to CNTF, the receptor for CNTF (originally termed "CNTFR") has been cloned, sequenced and expressed (see copending U.S. application No. 07/700,677, entitled "The Ciliary Neurotrophic Factor Receptor," filed May 15, 1991 and now abandoned by Davis, et al. and International Application No. PCT/US91/03896, filed Jun. 3, 1991 which are incorporated by reference in their entirety herein).

Unlike other known growth factor receptors which have an extracellular domain, a hydrophobic transmembrane domain and a cytoplasmic domain, the CNTF receptor does not appear to have a cytoplasmic domain. Furthermore, it is linked to the cell surface via a covalent linkage from the protein to an oligosaccharide which is in turn glycosidically linked to phosphatidylinositol (referred to as a "GPI-linkage"). GPI-linkages play a role in the attachment of proteins, such as alkaline phosphatase (APase) to membranes. The role of GPI linkages in the function of biological membrane components have been elucidated as a major means of anchoring proteins to biological membranes in the case of at least 30 distinct proteins. [(Slein, et al., J. Bacteriol. 80:77 (1960); Low, et al., Biochemistry 19:3913 (1980)].

Treatment of the cell-surface membrane of CNTF responsive cells with phosphatidylinositol-specific phospholipase C (PI-PLC) releases CNTFR from the cell membrane. Such release is prohibited, however, if CNTF is first bound to the receptor prior to exposure to the enzyme, indicating a possible interaction between CNTF, its receptor and a third, signal transducing component.

The discovery that CNTFR and CNTF may form a complex that interacts with a membrane bound, signal transducing component suggested therapeutic activity of a soluble CNTF/CNTFR receptor complex. In copending application U.S. Ser. No. 801,562 filed Dec. 2, 1991 by Yancopoulos, et al. entitled "Cell Free Ciliary Neurotrophic Factor/Receptor Complex", which is incorporated by reference in its entirety herein, CNTF and CNTFR are combined to form a stable, biologically active complex that can be used as a differentiation or proliferation factor in cell types that express signal transducing receptor components belonging to the CNTF/IL-6/LIF receptor family.

One such signal transducing component involved in high affinity binding of CNTF and the subsequent functional response of the cell has been identified as gp130, a β component common to the IL-6, Oncostatin M, LIF family of receptors. A further β component identified as being involved in binding and signal transduction in response to LIF (LIFRβ) appears to be the same or similar to a β component necessary for response to CNTF. (As a consequence of the identification of β components necessary for binding and signal transduction of CNTF, what was originally generally termed CNTFR is currently referred to as CNTFRα). Accordingly, as described in U.S. application Ser. No. 07/865,878 filed on Apr. 8, 1992 and now abandoned entitled "Cell-Free Ciliary Neurotrophic Factor/Receptor Complex", which is incorporated by reference in its entirety herein, signal transduction can be initiated by treatment of cells expressing both gp130 and LIFRβ with a soluble CNTF/CNTFRα complex. Alternatively, target cells not previously responsive to CNTF, but expressing LIFRIβ and gp130 (such as LIF-responsive cells) can be made responsive to CNTF by attaching the CNTFRα to the cells and subsequently treating with CNTF.

The molecular cloning of the coding region for human CNTFRα (hCTNFRα) enabled the generation of probes useful for detecting the presence of receptor message in a variety of tissues. The results of such studies indicated that CNTFRα mRNA was detectable in tissues of the central nervous system, sciatic nerve, adrenal tissue and in skeletal muscle. As described in copending application U.S. Ser. No. 07/700,677, now abandoned, entitled "CNTF Receptor" which is incorporated by reference in its entirety herein, a detailed analysis of the CNTF receptor expression in muscle indicated that the CNTF receptor is expressed in both myotube and myoblast muscle cell lines of either mouse or rat origin, as well as in both red slow-twitch soleus muscle and white fast-twitch extensor digitorum longus (EDL) muscle of the rat.

Further described in U.S. application No. 07/700,677, now abandoned, is the finding that CNTF receptor mRNA was increased in both soleus and EDL muscle in animals that were first denervated for 72 hours relative to their sham-operated contralateral controls.

SUMMARY OF THE INVENTION

Figure 1:
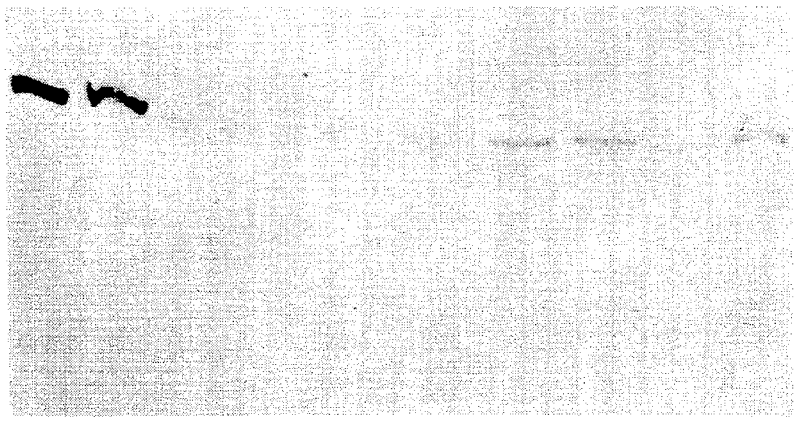
FIG. 1. CNTFRα levels in plasma increase after nerve crush in rats. Plasma (200 μl) from various post-surgical timepoints was extracted with biotinylated CNTF immobilized on streptavidin conjugated to agarose beads as described in the Example section. The figure shows an immunoblot developed with secondary antisera conjugated to alkaline phosphatase. Samples are 25 fmoles CNTFRα standard (lane 1), PBS spiked with 25 fmoles CNTFRα and extracted with immobilized CNTF as control (lane 2), rat plasma samples taken at the indicated time after nerve crush: 0 h (lane 3), 6 h (lane 4), 18 h (lane 5), 24 h (lane 6), 30 h (lane 7), 42 h (lane 8), 48 h (lane 9), 72 h (lane 10).

The present invention relates to methods of diagnosing, detecting or monitoring neurological and/or muscular injuries, disorders or diseases.

An object of the present invention is to diagnose injury or disorders or diseases of the muscle.

Another object of the invention is to diagnose injury or disorders or diseases associated with muscle denervation or degeneration.

A further object of the present invention is to monitor the progression of a neurological and/or muscular injury or disease or disorder.

Another object of the invention is to measure the effect of a particular treatment on a neurological or muscular disease or disorder.

These and other objects are achieved in accordance with the invention by measuring the amount of CNTFRα in a body fluid such as blood or urine.

DETAILED DESCRIPTION OF THE INVENTION

The present invention relates to a method of diagnosing diseases and disorders in human or animals in which muscle degeneration plays a role. It is based on the finding that CNTFRα message increases in denervated muscle and the further discovery that, under such circumstances, the receptor is shed. As described herein, the presence of the shed receptor in body fluids provides a means of monitoring or diagnosing nerve or muscle injury or degeneration by measuring the amount of soluble CNTFRα in body fluids.

Soluble cytokine receptors which bind IL-6 and IFN-γ have been reported in urine under normal physiological conditions [Novick, et al. J. Exp. Med. 170 (1989):1409-1414]. In addition, truncated nerve growth factor receptor occurs in urine of neurologically normal subjects during normal development. [DiStefano, et al. Annals of Neurology 29:13020(1991)]. Levels of truncated nerve growth factor receptor in the urine have been suggested as a means of determining the presence of nerve growth factor receptor bearing tumors [Johnson, E. U.S. Pat. No. 4,800,241 (1989)]. There is no indication that these, or any other receptors, are shed in response to muscle or nerve injury or disease.

As described herein, applicants have discovered a dramatic increase in the level of message for CNTF receptor in soleus muscle after nerve transection or crush. As innervation of the muscle was reestablished (in the case of the sciatic nerve crush), the level of CNTF receptor mRNA decreased.

Despite the increase in CNTF receptor message after crush, the amount of CNTFRα protein in denervated muscle tissue did not appear to increase commensurately. In view of the readily cleavable GPI membrane anchor of CNTFRα, this suggested the possible release of the receptor into surrounding blood. Applicants subsequently discovered that the dramatic increase in the level of the CNTF receptor mRNA in response to nerve crush or injury appeared to be reflected by the presence of an elevated level of the encoded CNTF receptor in a body fluid.

According to the present invention, an elevated level of CNTFRα in body fluid such as blood, plasma, urine or cerebral spinal fluid of a patient relative to the level of such receptor in a normal subject is used as an indicator that the patient is afflicted with some form of muscle degeneration. Such degeneration may be caused by an injury, by a degenerative muscle disease or disorder, or by a disease, disorder or damage to the nervous system which results in denervation of muscle. Such diseases or disorders include, but are not limited to, degenerative or inflammatory muscle diseases such as muscular dystrophy, myotonic dystrophy, fascio-scapulo-humoral dystrophy, limb girdle dystrophy, distal muscular dystrophy or myositis or peripheral neuropathies associated with diabetic neuropathy, acute neurapraxia, neurotmesis or axotmesis. In addition, the methods described herein can be used to diagnose or monitor neurological degenerative diseases, especially those associated with degeneration of motor neurons, such as amylotrophic laterial sclerosis, spinal muscular atrophy, post-polio syndrome, infantile muscular atrophy, poliomyelitis or Charlot-Marie Tooth disease or inflammatory or demyelinating neurological diseases or disorders such as Guillan-Barre Syndrome or chronic inflammatory demyelinating polyneuropathy. The methods of the present invention may also be used to diagnose or monitor degeneration caused by nerve injuries such as those associated with carpal tunnel syndrome, compression, mechanical severance of a nerve or a tumor. In addition, the methods disclosed herein may be utilized to diagnose neural or non-neuronal tumors.

The present invention contemplates not only diagnosis, but also monitoring of the progression of a neurological and/or muscular disease or disorder, or the effect of a particular treatment on the progression of such a disease or disorder. In such cases, the level of CNTFRα in the body fluid is monitored over a set period of time. The efficacy of a particular treatment is determined by comparing the level of receptor in the body fluid of an afflicted individual receiving treatment with the level of receptor in the body fluid of a comparable patient not receiving such treatment.

The level of CNTFRα in any body fluid of an afflicted patient may be measured and compared to the comparable level of such receptor in a normal patient. Preferably, the body fluid analyzed is urine, blood or cerebral spinal fluid. Analysis of urine may require normalization to account for individual variation; one such method involves normalization to the urine level of creatinine, an established indicator of the variable water content between individual samples [DiStefano, et al. Annals of Neurology 29: 130-20(1991)].

CNTFRα levels in plasma may be preferable in that normalization is generally not required. Purification and concentration may be accomplished by any number of methods known to those in the art; as described herein, a simple method of accomplishing such purification and concentration involves the use of biotinylated CNTF.

Analysis and quantitation of CNTFRα is exemplified herein by immunoblotting with an antibody raised and immunopurified against CNTFRα, such as, for example, antibodies raised against a peptide corresponding to the N-terminus of human CNTFRα. Alternatively, monoclonal antibodies, such as those produced using the method of Kohler and Milstein [Nature 256, 495–497 (1975)], may be used.

Immunoreactive proteins may be visualized using antibodies produced against the CNTFRα antibodies which are conjugated to an indicator such as alkaline phosphatase or $^{125}I$, which enables quantitation of reactive bands. Other immunoassay procedures known to those in the art, such as radioimmunoassays or enzyme-linked immunosorbent assays (ELISA), can also be used in the method of the present invention.

EXAMPLES

Example 1. Regulation of CNTF Receptor (CNTFR) mRNA in Deafferented Muscle

Significant levels of CNTFR mRNA can be detected in normal skeletal muscle. To determine whether this CNTFR mRNA is regulated in response to altered nerve/muscle interactions, the levels in muscle following sciatic nerve transection or crush were examined.

1.1 Methods

Experimental subjects and surgical methods were as follows: Sciatic nerves of adult male Sprague-Dawley rats were cut or crushed at the level of the sciatic notch. In nerve transection experiments, nerves were transected and the distal stump turned back and tucked under overlying musculature. This procedure effectively prevented regeneration of the cut nerves. Nerve crush was produced by tightly compressing the sciatic nerve with a #5 jewelers forceps for ten seconds; this technique caused axons to degenerate distal to the crush but allowed subsequent regeneration of the nerve. Soleus muscle was dissected from normal or operated rats at different times after transection or crush of the sciatic nerve. Total RNA was prepared by the lithium chloride precipitation method, and the CNTFR transcripts analyzed by immunoblotting with an antibody (RG30) raised and immunopurified against a peptide corresponding to the N terminus of human CNTFR. A vector encoding the entire human CNTFR sequence was deposited under the terms of the Budapest Treaty with the Agricultural Research Service Culture Collection in Peoria, Illinois on Mar. 26, 1991 and assigned NRRL B-18789.

1.2 Results

One day following transection of the sciatic nerve, there was a striking increase in the level of CNTFR mRNA in soleus muscle. This increase was substantially attentuated 2 days after the lesion, but increased again slowly and progressively over 122 days. A dramatic increase in CNTFR mRNA also was observed one day following nerve crush, followed by a relative decrease. A subsequent progressive increase in CNTFR mRNA levels was seen over the first post-operative week. However, in marked contrast to the transection condition in which regeneration of the nerve was prevented, the level of CNTFR mRNA in muscle denervated by crush stabilized in the second post operative week and subsequently decreased as innervation of the muscle was re-established.

The normally high constitutive expression of CNTF receptor mRNA in the CNS was unaltered by trauma (data not shown).

In contrast to the increased level of CNTFR mRNA found after injury, no corresponding increase in the level of CNTFR protein was observed on the membrane surface. This suggested the possibility that receptor was released from the cell surface into surrounding body fluid.

EXAMPLE 2. Detection of CNTFRα in Body Fluid 2.1 Methods 2.1.1 Preparation of Biotinylated CNTF (bCNTF)

CNTF (150–400 mg in PBS, pH 7.4) was incubated with a 5-fold molar excess of NHS-LC-biotin (Pierce, typically dissolved to 5 mg/ml in PBS immediately before use) in a volume of 500 μL or less for 2 hours at 4 C. The reaction was quenched by the addition of 50 μL 3 M Tris, pH 8.2, for approximately 15 minutes.

Biotinylated mono and dimeric CNTF were purified and separated from excess biotinylation reagent by chromatography on a Superdex 75 HR 10/30 column (Pharmacia) using a Pharmacia FPLC system pumping PBS at a flow rate of 1 ml/min. Dimer and monomer bCNTF elute at times of 10 and 12 minutes respectively. Protein concentration and recovery were determined by optical density readings at 280 nm using an extinction coefficient of $e=2.05\times10^4$ cm-1 M-1, therefore a solution containing 1 mg/ml has an absorbance of 0.9. The fraction of unbiotinylated CNTF in the preparation was evaluated by first boiling about 1 mg of the bCNTF in a buffer containing 50 mM Tris (pH 8.2) and 1% SDS, and then incubating the sample with an excess amount of streptavidin-agarose beads (SA-agar; Sigma) for 1 hour at room temperature. A parallel sample was prepared with SA-agar that has been saturated with excess biotin prior to addition of bCNTF. The beads are removed by centrifugation, and the supernatant fractions are analyzed for unbound CNTF by silver staining following SDS PAGE. Typically greater than 90% of the CNTF becomes biotinylated by this procedure.

2.1.2 Preparation of bCNTF:SA-agar Complex and Extraction of CNTFRa from Plasma or Urine Biotinylated CNTF in PBS was incubated with SA-agar beads at a molar ratio of 1:3 (bCNTF: biotin binding capacity of the SA-agar) for 1 hour at room temperature. The beads were washed exhaustively with PBS, then resuspended in PBS to their original volume. A 200 μl aliquot of plasma (prepared in EDTA to prevent clotting) was diluted to 500 μL in PBS containing 5 mM EDTA, 1 mM PMSF, $4.8\times10^{-2}$ TIU aprotinin/ml and 0.1 mg pepstatin A/ml, then incubated with 50 ml of the resuspended bCNTF-SA-agar complex for 2 hours at room temperature on a labquake mixer. The beads were washed once with PBS, then the captured proteins were released by boiling in SDS PAGE sample buffer and analyzed by immunoblotting with a rabbit antibody (RG30) raised and immunopurified against a peptide corresponding to the N-terminus of human CNTFRα. Immunoreactive proteins were visualized with goat anti-rabbit Ig conjugated to either alkaline phosphatase or $^{125}I$. Use of the radioactive secondary reagent permitted quantitation of the reactive CNTFRα bands with the Fuji Biolmager. Control experiments using recombinant CNTFRα released from fibroblasts with phospholipase C (which cleaves the GPI anchor to give a soluble protein) indicated recoveries of 50–80% and a nearly linear response over a >10-fold concentration range (e.g. FIG. 1, lanes 1 and 2).

Urine samples were analyzed using a similar method on a larger scale. Quantitation of urine samples required normalization to the urine level of creatinine, an indicator of the variable water content between individual urine samples.

2.2 Results 2.2.1 Analysis of CNTFRα in plasma after sciatic nerve crush

Analysis of plasma following bilateral sciatic nerve crush in the rat revealed a transient increase in the amount of CNTFRα in the blood (FIG. 1). Various experiments revealed that the level of CNTFRα peaked between 30–48 hours after injury and generally fell by 72–80 hours, lagging slightly behind the increase observed in the muscle mRNA level. Quantitation of CNTFRα in experiments with iodinated secondary reagents showed that this increase measured about 5-fold above the control level.

2.2.2 Analysis of CNTFRα in Urine from Control and Denervated Rats

Analysis of the urine from control and denervated rats revealed the same trend as above for plasma: normal animals had a low or undetectable level of urine CNTFRα, which rose significantly by 48 hours after denervation. The migration of the CNTFRα in the gel was close to that of the phospholipase-cleaved standard, indicating that the GPI diacylglycerol had been cleaved, or that the entire GPI had been removed. The soluble CNTFRα appeared to be functional as it retained the ability to bind CNTF.

2.2.3 Analysis Of CNTFRα in urine from ALS patients

Figure 2:
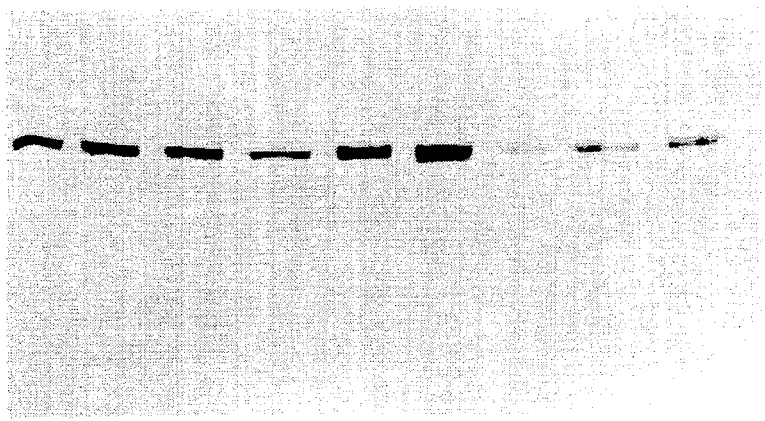
FIG. 2. CNTFRα in urine from normal humans and patients with ALS. Urine samples (1 ml) were brought to neutral pH and incubated with biotinylated CNTF to extract CNTFRα as described in the Example section, then analyzed by immunoblotting. Lane 1 is 12.5 fmole of recombinant CNTFRα, and lane 2 is ALS urine spiked with 12.5 fmole of CNTFRα. Lanes 3-6 are urine samples from ALS patients while lanes 7-10 are urine samples from unafffflicted individuals.

Given the striking increase in the level of CNTFRα in blood and urine upon denervation in rats, we tested whether humans suffering from ALS, in whom progressive muscle denervation occurs, might also display increased CNTFRα levels. Urine from 4 patients with ALS was analyzed by the method outlined above, and compared to the amount of CNTFRα observed in 4 unafflicted subjects(FIG. 2) Although all individuals excreted detectable amounts of CNTFRα in their urine, ALS patients exhibited elevated levels relative to the levels found in the unafflicted subjects. (FIG. 2, lanes 3–6).

Table 1 reveals that the ALS patients as a group had a 4.3-fold elevation in urine CNTFRα relative to the control group. A t-test of these values indicates the groups are statistically different at the level of $P<0.02$. In contrast, the level of creatinine between the two groups was not statistically different.

TABLE 1

Quantitation of creatinine and CNTFRα in human urine

| | Creatinine (mg/ml) | CNTFRα (ng/ml) | CNTFRα/Creatinine (ng/mg) |
|---|---|---|---|
| ALS #1 | 1.17 | 10.7 | 9.15 |
| ALS #2 | 1.80 | 13.2 | 7.33 |
| ALS #3 | 0.29 | 5.6 | 19.3 |
| ALS #4 | 0.77 | 14.9 | 19.4 |
| Mean + S.D. | 1.01 + 0.64 | | 13.8 + 6.5 |
| Norm #1 | 0.16 | 0.5 | 3.2 |
| Norm #2 | 2.47 | 12.9 | 5.2 |
| Norm #3 | 1.38 | 4.8 | 3.5 |
| Norm #4 | 1.19 | 0.9 | 0.8 |
| Mean + S.D. | 1.29 + 0.95 | | 3.2 + 1.8 |

We claim:

1. A method of detecting muscle denervation in a patient afflicted with such muscle denervation comprising:
   a) obtaining from said patient a sample of a body fluid;
   b) reacting said sample with a material which specifically binds to ciliary neurotrophic factor receptor alpha protein (CNTFRα) which is present in solution in said sample to provide a complex of CNTFRα and said material;
   c) determining a level of CNTFRα in said sample based on a measurement of said complex;
   d) comparing the level of CNTFRα determined in said sample to levels of soluble CNTFRα determined in samples of the body fluid of unafflicted individuals, wherein an elevated level of CNTFRα in the sample is indicative of muscle denervation in the patient.

2. The method of claim 1 wherein said muscle denervation is associated with a motor neuron disease or disorder.

3. The method of claim 2 wherein said motor neuron disease is amyotrophic lateral sclerosis.

4. The method of claim 1 wherein said muscle denervation is associated with nerve injury.

5. The method of claim 1 wherein said body fluid is urine, blood or plasma.

6. The method of claim 1 wherein said material is an antibody specific for CNTFRα.

* * * * *

UNITED STATES PATENT AND TRADEMARK OFFICE
Certificate

Patent No. 5,360,740                                    Patented: November 1, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nancy Y. Ip, Stamford, Conn.; Peter S. DiStefano, Carmel; Neil Stahl, Carmel; and Thomas J. Farruggella, Chester, each of N.Y.

Signed and Sealed this Third Day of November, 1998.

PAULA K. HUTZELL, PH.D.
*SPE*
Art Unit 1817